(12) United States Patent
Wyatt et al.

(10) Patent No.: US 7,162,161 B2
(45) Date of Patent: Jan. 9, 2007

(54) OPTICAL COMMUNICATIONS SYSTEM AND METHOD OF PROTECTING AN OPTICAL ROUTE

(75) Inventors: Richard Wyatt, Woodbridge (GB); Robert M. Percival, Ipswich (GB); Raman Kashyap, Ville Saint Laurent (CA)

(73) Assignee: British Telecommunications public limited company, London (GB)

( * ) Notice: Subject to any disclaimer, the term of this patent is extended or adjusted under 35 U.S.C. 154(b) by 882 days.

(21) Appl. No.: 09/805,377

(22) Filed: Mar. 14, 2001
(Under 37 CFR 1.47)

(65) Prior Publication Data
US 2002/0141021 A1    Oct. 3, 2002

(30) Foreign Application Priority Data
Mar. 24, 2000   (EP)   ..................... 00302423

(51) Int. Cl.
*H04B 10/12*   (2006.01)
(52) U.S. Cl. ........................ 398/142; 398/139
(58) Field of Classification Search ............. 398/141, 398/9, 186, 139, 142; 385/28, 50
See application file for complete search history.

(56) References Cited

U.S. PATENT DOCUMENTS

| 4,867,518 | A |   | 9/1989  | Stamnitz et al. |
|-----------|---|---|---------|-----------------|
| 4,913,507 | A |   | 4/1990  | Stamnitz et al. |
| 4,973,125 | A |   | 11/1990 | Normandin |
| 5,434,942 | A |   | 7/1995  | Jackel et al. |
| 5,463,708 | A | * | 10/1995 | Yui et al. .................... 385/49 |
| 5,594,825 | A | * | 1/1997  | Kawasaki et al. ............ 385/60 |
| 6,014,396 | A |   | 1/2000  | Osinski et al. |
| 6,049,558 | A | * | 4/2000  | Harada et al. .............. 372/107 |
| 6,590,698 | B1| * | 7/2003  | Ohtsuki et al. ............. 359/326 |

FOREIGN PATENT DOCUMENTS

| EP | 1 139 521   | * | 10/2001 |
| WO | WO 9946835  | * | 9/1999  |

* cited by examiner

*Primary Examiner*—David C. Payne
(74) *Attorney, Agent, or Firm*—Nixon & Vanderhye, P.C.

(57) ABSTRACT

A section of tapered optical fiber is provided to protect optical components from catastrophic damage that may propagate within an optical route. The tapered section functions as a fuse to arrest the propagation of optical power induced damage by leaking optical power from a waveguiding region below a threshold, below which further propagation of damage is not supported.

23 Claims, 6 Drawing Sheets

Velocity of damage propagation as a function of power in core for three fibres, A, B & C. There is a linear dependence on the input power, but it varies for each fibre and wavelength.

Fig.8.

Measured (data points) and calculated (continuous curves) velocity of damage propagation in two types of silica fibre, 'A' & 'B' at 1.604 μm and 0.514 μm. The absorption factors used in the calculations are shown. The slopes are sensitive to the choice of the absorption factor.

OPTICAL COMMUNICATIONS SYSTEM AND METHOD OF PROTECTING AN OPTICAL ROUTE

BACKGROUND OF THE INVENTION

1. Field of the Invention

The present invention relates to an optical communications system, and devices for use in such a system, and methods of protecting an optical route. In particular, but not exclusively, the invention relates to an optical fuse for protecting network components in the route.

2. Description of Related Art

Optical communication routes are known including optical waveguides, such as optical fibres and optical components, such as lasers and optical amplifiers. Such routes have a huge information-carrying capacity.

It is known that an optical route can suffer damage as a result of power surges. For example, routes which include rare earth doped optical amplifiers can suffer damage. In particular, when a rare earth doped optical amplifier goes from a state in which no signal is being input to a state in which an input signal is received, the device may output a surge of power. Under certain circumstances such power surges may cause damage to the route including the amplifier and devices downstream of the source of the power surge.

In such circumstances, it may be necessary to protect optical routes from power surges.

EP 0 943 954 proposes a solution to this particular problem. An optical fuse is provided, which is disposed in an optical route, and operates along principles similar to an electrical fuse. The fuse is arranged to "blow" when optical radiation travelling in a downstream direction away from an optical source, incident on the fuse is in excess of a preselected threshold level chosen by the route operator. The threshold is set so that under normal operating conditions the fuse will not "blow", but will "blow" in the event of a power surge.

Once the fuse has "blown", the power surge radiation can no longer propagate beyond the "blown" fuse. The fuse is disposed between two optical fibres, and includes a first layer which heats up on exposure to optical radiation and a second layer which, depending on which material is chosen, loses its transparency or reflectivity, respectively, when heated. The layers are dimensioned and arranged so that when optical radiation above the preselected threshold is incident on the first layer, sufficient heat is generated to cause the second layer to lose its transparency or reflectivity, depending on the material chosen. Thus, the optical signal can no longer propagate from the first to the second optical fibre. The fuse cannot be reset. Once the fuse has "blown" it must be replaced before the route can work normally. Provided the power level remains below the preselected threshold level the fuse remains transparent or reflective, thus allowing the further propagation of an optical signal.

One drawback of the fuse proposed in EP 0 943 954 is that the devices are complex to fabricate. Further, the fuse described in EP 0 943 954 has been designed for the particular application described above of arresting the propagation of a power surge. However, it has been found that in addition to power surges, an optical fibre carrying an optical signal may be subject to other optical phenomena that may damage the fibre.

As a result of an optical communications route's huge information-carrying capacity, there is a growing demand on optical communications routes to carry an increasing amount of information. There is therefore much interest in developing methods for increasing the transmission capacity for optical routes. One method is wavelength-division multiplexing (WDM), in which several data channels, at different wavelengths, are carried simultaneously on the same fibre. Thus, the information carried by the waveguide, and also the amount of power transmitted by the waveguide is increased in accordance with the number of channels carried by each fibre.

Although, it is known, that optical waveguides are able to transmit high power signals without suffering any damage, it has been found that an optical waveguide may undergo catastrophic self propagating damage if, whilst transmitting a high power signal, it is subject to an external stimulus. Such stimuli are discussed in Electronics Letters, 2 Mar. 2000, vol. 36, no. 5, pages 414–416, and may, for example, be breaking or cutting of the waveguide, but may also be some externally applied mechanical shock which does not itself interrupt the fibre path, such as for example, bending the optical fibre. This effect is called "self propelled self focussing damage", and is the subject of EP 0 309 234. The mechanism may be started by accidental damage to a fibre cable carrying in excess of approximately the order of 1 Watt of optical power, and has been seen when a broken fibre end comes into contact with an absorbing surface. The damage can be observed as a blue-white plasma-like localised emission which travels at a velocity of tens of centimeters per second or higher in an upstream direction back along the fibre towards the source of the optical power. The power required to sustain the propagation of the damage is "fuelled" by the optical signal. The damage will thus propagate along the fibre in a direction towards the source of the optical signal, feeding on the optical signal. The damage will continue to propagate as long as the fibre carries a signal having a power above approximately the order of 1 Watt (the precise power level required to cause and sustain such damage depends upon the properties of the fibre). In WDM systems, the combined optical power of the data channels may be above 1 Watt. As mentioned above, damage may occur if a fibre transmitting more than approximately 1 Watt is subject to an external stimulus, and hence, there exists a real risk of this catastrophic damage in such WDM systems.

One disadvantage of the optical fuse described in EP 0 943 954 is that it would not be suitable in the situation described above. The fuses in EP 0 943 954 are suitable for arresting an optical power surge travelling in a downstream direction from damaging any optical components disposed downstream of the origin of the power surge. They are designed to blow when an optical amplifier experiences a surge in optical power. They are designed not to blow under operating conditions at which the optical route was designed to operate. Self propelled self focussing damage however, occurs at normal high power transmission conditions and results in catastrophic damage to the optical route which propagates in a direction upstream of the origin of the self propelled self focussing damage.

A fuse suitable for arresting damage must not blow at the operating optical power of the system, but must prevent propagation of damage beyond the site where the device is located should damage occur.

Although, it is likely that the fuse of EP 0 943 954 would blow if it were subject to catastrophic damage, it is not suitable because it would not arrest the damage because the source of optical power fuelling the damage would not be interrupted. Indeed, the fuse of EP 0 943 954 might even initiate self propelled self focussing damage due the heat generated when it blows as the result of a downstream propagating power surge. Whilst the damage propagated through the fuse, it would continue to be fuelled by the optical signal being transmitted in a downstream direction in the opposite direction from the propagating damage. The damage would not be arrested until the optical signal was turned off. The only solution would be to ensure that the systems in which the fuses of EP 0 943 954 operated at optical powers below the threshold power above which catastrophic damage occurs. As a result of the increased demand for higher capacity on optical fibres, operating optical communication routes below this threshold may not always be desirable.

U.S. Pat. No. 4,973,125 discloses a self limiter for fibre optics. The limiter includes a semiconductor optoelectronic device. Between the device and the system fibre an air gap is provided. The size of the gap determines the self limiting effect provided. U.S. Pat. No. 6,014,396 discloses a flared semiconductor optoelectronic device. The devices disclosed in U.S. Pat. Nos. 4,973,125 and 6,014,396 suffer from the disadvantage that the semiconductor devices must be packaged in such a way to enable their integration into the optical fibre system. Further, U.S. Pat. No. 6,014,396 suffers from the additional disadvantage that the device must be constructed and packaged in such a way that the dimensions of the air gap are accurately established and maintained.

BRIEF SUMMARY OF THE INVENTION

The present invention seeks to provide a device which permits the transmission of optical signals under various operating conditions but arrests catastrophic damage that may occur to the fibre.

In accordance with a first aspect of the present invention, there is provided an optical communication system including an optical communications route comprising system fibre or a laser pigtail fibre having a given mode field radius at an operating wavelength of the system, an optical route component for performing a function within the optical system, said optical route component forming part of the optical communications route and being connected to the system fibre or the laser pigtail fibre, and enclosed in a sealed container, the optical route component providing an optical output which passes along the system fibre or the laser pigtail fibre from the container, the output of the optical route component passing through a mode field transformer and thence along the system fibre or the laser pigtail fibre, the mode transformer including a section of optical fibre disposed at a location downstream of said container and serving to increase locally the mode field radius at said wavelength, the optical system being operated with an optical power density in the system fibre or the laser pigtail fibre above a level at which optical power induced damage can propagate in the system fibre or the laser pigtail fibre, the mode transformer reducing the optical power density for said given power level such that within the mode transformer the power density is reduced below the threshold level, so that in the event that optical power induced damage occurs in the system fibre or the laser pigtail fibre downstream of said mode transformer the damage is prevented from propagating into the optical route component.

Thus, in accordance with the invention, the route components disposed in the path of the propagating optical power induced damage are protected.

In accordance with a second aspect of the present invention, there is provided an optical device for use in a system, said device including an optical route component for performing, in use, a function within the optical system, and being enclosed in a sealed container, the optical route component having a fibre pigtail for connection to a downstream optical fibre of said system, the optical route component providing an optical output having in said fibre pigtail a given mode field radius at an operating wavelength of said device; the device further including a mode field transformer a mode field transformer including a section of optical fibre, the mode field transformer being disposed at a location downstream of said container between said container and said fibre pigtail, said mode field transformer having a mode field radius at said wavelength substantially larger than said given mode field radius and being sufficiently large to reduce at said location the optical power density of said optical output to below the threshold level at which optical power induced damage can occur in said pigtail fibre downstream of said mode field transformer, thereby, in the event that optical power induced damage occurs in the pigtail fibre, preventing the damage from propagating into the optical route component.

In accordance with a third aspect of the present invention, there is provided an optical communications route comprising a deployed system fibre at least 100 meters in length, the system having fibre having a given mode field radius at a given wavelength at which the fibre is designed to operate, said system fibre being provided with a mode field transformer at each end of said fibre, each mode field transformer having at said wavelength a mode field radius at least three times said given mode field radius.

In accordance with a fourth aspect of the present invention, there is provided a plurality of mode field radius transformers disposed in an array, being arranged in use, so that each mode field transformer is connectable or spliceable with a respective system fibre in which at a given wavelength the mode field radius of an optical signal is x, each mode field radius transformer being arranged to increase the mode field radius of said optical signal, with respect to x, so that the power density of said optical signal in said mode field transformer is reduced to a level below the threshold required for optical power induced damage to propagate within the mode field transformer.

According to a fifth aspect of the invention, there is provided a method of protecting an optical communications route carrying a high power optical signal from catastrophic damage caused by the propagation of optical power induced damage along said route, said method including the steps of:
identifying a site where optical power induced damage is likely to be initiated and the likely path of damage propagation,
selecting a route component to be protected, disposed in said path, disposing a mode field radius transformer at a location in said optical communications route between said identified site and said selected component, the optical communications route having an optical fibre transmission path connecting said site and said component, the optical fibre having a given mode field radius at an operating wavelength of the signal, the power density of said optical signal in said fibre being at a level at which optical power induced damage can propagate in said fibre, said mode field radius transformer including a section of optical fibre to increase substantially the mode field radius with respect to said given mode field radius so that the optical power density in the mode field transformer is reduced to a level at which optical power induced damage cannot propagate through the mode field transformer, so that
optical power induced damage will be halted at said location before reaching said component.

According to a sixth aspect of the invention, there is provided a method of protecting an optical communications route carrying a high power optical signal from the propagation of optical power induced damage along the route, the route including an optical device including a route component for performing a function within the optical route, said route component being housed in a container, said method including the step of:

providing an optical fibre section at a location in said optical communications route outside said container, the optical fibre section being so dimensioned as to decrease the optical power density within said optical fibre section to a level below that at which catastrophic damage propagation is supported, so that optical power induced damage propagating in the route immediately downstream of said location will be halted at said location before reaching said container.

According to a seventh aspect of the invention, there is provided a use of a mode field transformer including a section of optical fibre to provide a significant localised increase in mode field radius from that of adjacent system fibre to serve as a barrier to the propagation of optical power induced optical damage from the system fibre through the mode field transformer.

BRIEF DESCRIPTION OF THE DRAWINGS

In order that the invention may be more fully understood embodiments thereof will now be described by way of example, and by way of contrast with a prior art device as previously described, reference being made to the accompanying drawings in which.

DETAILED DESCRIPTION OF EXEMPLARY EMBODIMENTS

Figure 1:
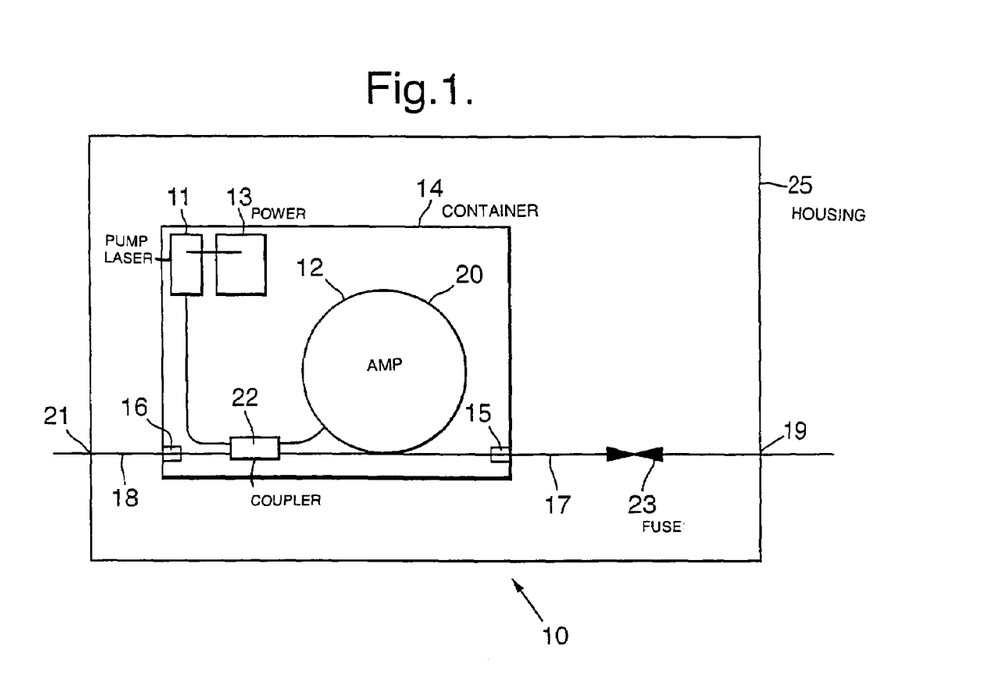
FIG. 1: shows an optical device according to the present invention.

Referring to the drawings, FIG. 1 shows an optical device 10 including an optical component 12 housed in a container 14. The optical component 12, in FIG. 1 is a conventional packaged optical amplifier. The active element 20 comprises a length of erbium doped fibre, typically several meters long coiled on a mandrel (not shown). A pump laser 11, and a power supply 13 for the pump laser 11 are also provided. The output from the pump laser is fed into a multiplexing coupler 22 and, via the coupler is introduced into the length of erbium doped fibre in a clockwise direction. The output from the coupler carrying the pump light is fusion spliced to the length of erbium doped fibre. Light from the pump laser 11 in the length of doped fibre 20 excites the erbium atoms, raising them to a higher energy level.

The optical signal to be amplified is fed into the optical amplifier at input 18. An optical isolator 16 is provided at the input to prevent scattered light from being input to the amplifier. The optical signal to be amplified is coupled via the multiplexing coupler 22 into the length of doped fibre 20. The pump light and the signal copropagate in the length of erbium doped fibre. The input optical signal to be amplified stimulates the excited erbium atoms to emit their excess energy as light at the signal wavelength, and in phase with the input optical signal. The amplified signal exits the amplifier via output 17. An optical isolator 15 is provided at the output 17 to prevent scattered light from entering the amplifier. Any pump light is prevented from leaving the amplifier via the input, by a filter (not shown) disposed between the coupler 22 and the length of doped fibre 20.

It will be understood that the performance of the fibre amplifier may be affected by environmental conditions, such as temperature, humidity. Further, the performance may be affected by physical disturbances. For these reasons, it is usual to provide the fibre amplifier within a container 14, typically sealed, preferably hermetically sealed. In FIG. 1, power supply for pump laser and pump laser are depicted as being disposed within the container 14. However, in some applications, such as amplifier for use in undersea cables, it is preferable to dispose a pump laser and power supply at a remote location. Thus far, the described optical device is conventional.

The optical device 10 in FIG. 1 is further provided with a mode field radius transformer 23, which may take the form of a section of optical fibre, which functions as a fuse to protect the optical component 12 housed by container 14 from catastrophic damage propagating towards the optical component 12.

As is well known in an optical fiber light is guided by the fibre core but in practice the light travels in the core and in the immediately adjacent cladding, the optical intensity typically varying according to an approximately Gaussian distribution across the fibre from a peak within the fibre core. For single mode fibres, if the radial field distribution of the fundamental mode is assumed to be exactly Gaussian, the spot size is the distance from the fibre axis at which the field amplitude is $1/e=0.37$ and the intensity $1/e^2=0.135$ of the corresponding values on the axis. The mode field diameter is twice the spot size. Using this convention, the mode field radius has the same value as the spot size. The mode field width is another term for the mode field diameter.

For given fibre parameters, the mode field radius can be increased if the core diameter is reduced sufficiently. This may be achieved, for example, by providing a waist portion in a section of optical fibre. Increasing the mode field radius will, for a given power level, reduce the power density. The inventors of the present invention have applied this knowledge to the problem of self-focusing catastrophic damage and have realised that it is possible to provide a means to limit the propagation of such damage. By incorporating a section of fibre having a waist portion having a sufficiently small core diameter or cross sectional area, at an appropriate point in a transmission link, it is possible to halt at that point any self-focusing catastrophic damage which reaches that point. However, during routine operation, high power levels can pass through the point without any power-limiting effect (in contrast with optical fuses of the type taught in EP-A-0 943 954).

Conveniently, the reduced diameter core section is provided by a waist portion in a section of optical fibre. The waist portion may be formed in a section of conventional fibre (typically by pulling the fibre while the fibre is softened by heat). Alternatively, however, a section of special fibre (or other suitable form of optical waveguide) with a large mode field radius is positioned between system fibres at the appropriate point.

Catastrophic damage, also called self propelled self focussing damage is a thermally driven phenomenon and has the effect of irreparably damaging the core of kilometer lengths of fibre. The phenomenon is discussed in two papers by Raman Kashyap, "Self-propelled Self-focussing damage in optical fibres", Proceedings of the International Conference on Lasers '87, Dec. 7–11, 1987, pages 859–866 and Electronic Letters, Jan. 7, 1988, vol. 24, no. 1, pages 47–49. It is known that at optical power densities of 1.5–2MW/cm$^2$, which is equivalent to an optical power of the order of 1 Watt in a single mode fibre, self propelled self focussing catastrophic damage may occur in optical fibres. The damage results in the formation of regular cavities in the core of the optical fibre having dimensions of the order of a few micrometers.

The threshold optical power density above which catastrophic damage may occur differs depending on the optical fibre. In particular, the optical density threshold is a function of the heat diffusion time constant of the particular optical fibre, which is inversely proportional to the square of the mode field radius of the optical signal transmitted by the particular fibre. The mode field radius of an optical signal transmitted by a particular fibre is determined by certain properties of the fibre and by the wavelength of the radiation transmitted in the optical signal. For a particular fibre, the mode field radius for a signal having a particular wavelength is determined by the refractive index profile of the optical fibre, the maximum difference in refractive index between the core and the cladding of the optical fibre, the diameter of the core. The refractive index profile describes how the refractive index of the fibre differs as a function of the distance from the centre of the fibre, and may, for example, be stepped or change at a constant rate.(triangle).

In the examples shown below single moded silica fibre was taken. The skilled person would understand that multimode fibre and optical fibres having different compositions would have different characteristics.

Two fibres A and B were taken to compare propagation characteristics. The characteristics of each fibre A and B are shown in Table 1. Several measurements were made with a Nd:YAG laser operating at 1.064 micrometers, both continuous wave and mode locked at average power levels varying between 0.7 and 2.4 Watts. With an argon laser operating at 514 nanometers measurements were also made on fibre B for continuous wave operation of powers ranging between 0.5 to 2.25 Watts As mentioned previously, catastrophic propagation may be initiated by an external stimulus. This may be heating, but may also include a mechanical shock to the fibre. For the data shown in Table 1 and shown in FIGS. 6 and 7, the catastrophic damage was initiated by either using an arc fusion jointing machine to generate a high temperature at the output end of the fibre whilst carrying an optical signal having a power in the range detailed above, or by contacting the end of the fibre with an absorbing surface. The catastrophic damage caused by an optical signal from the Nd:YAG laser at 1.064 micrometers is observed as an intense blue-white localised filament propagating towards the laser source. The damage caused by radiation from an argon laser at 514 nanometers is visible as a plasma like emission through argon line blocking safety glasses.

TABLE 1

Parameter data for fibres A and B.

| Fibre | Profile | Peak delta n | Core diameter (micrometers) | Mode field radius (at wavelength) |
|---|---|---|---|---|
| A | Step | $4 \times 10^{-3}$ | 8.05 | 6.04 (1.064 um) |
| B | Triangle | $5.48 \times 10^{-3}$ | 5.40 | 4.86 (1.064 um) |
| B | Triangle | $5.48 \times 10^{-3}$ | 5.40 | 3.30 (514 mm) |

Figure 7:
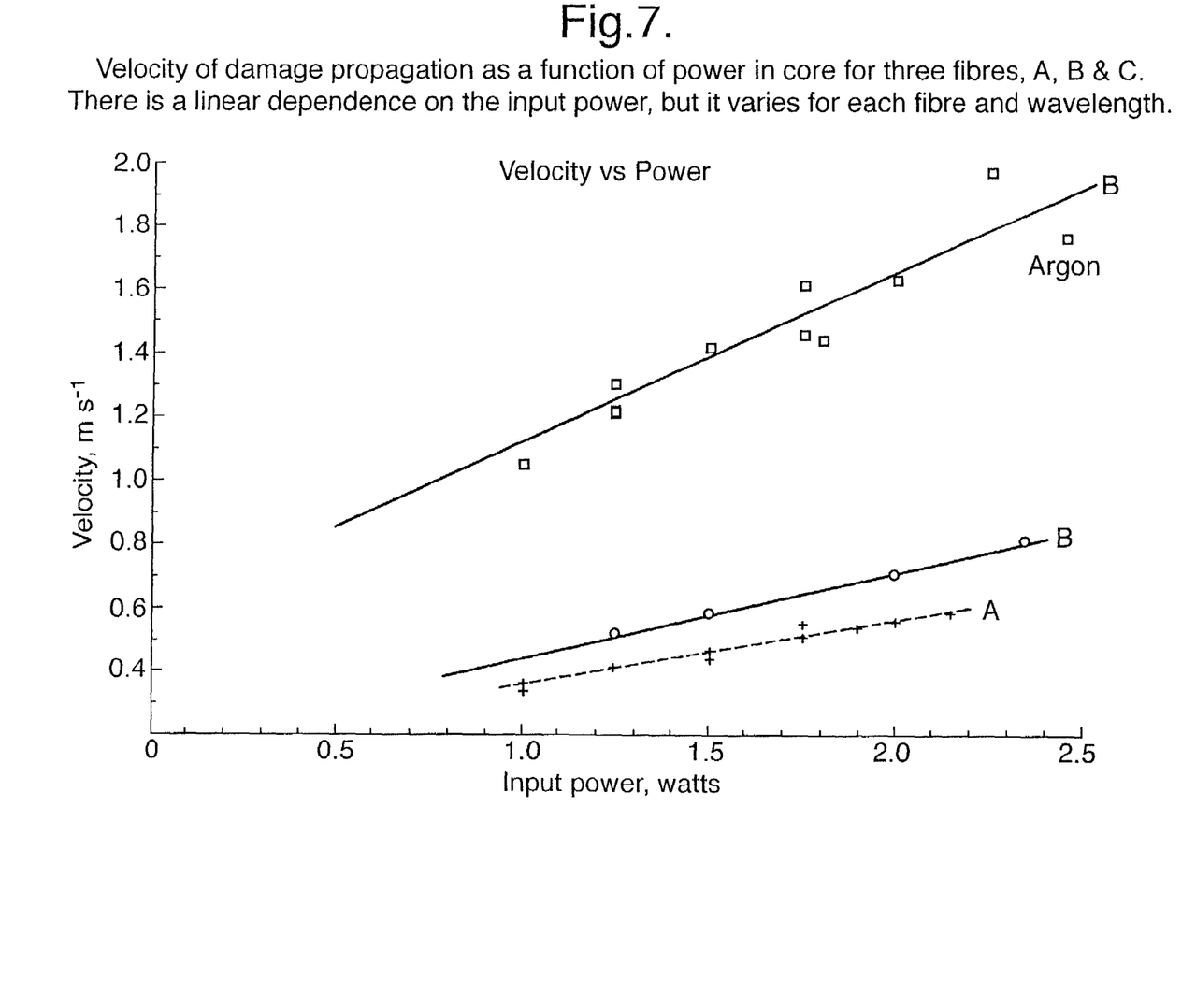
FIG. 7: shows how the velocity of catastrophic damage propagation varies as a function of optical power of the signal transmitted in an optical fibre, for three fibres, A, B and C.
Figure 8:
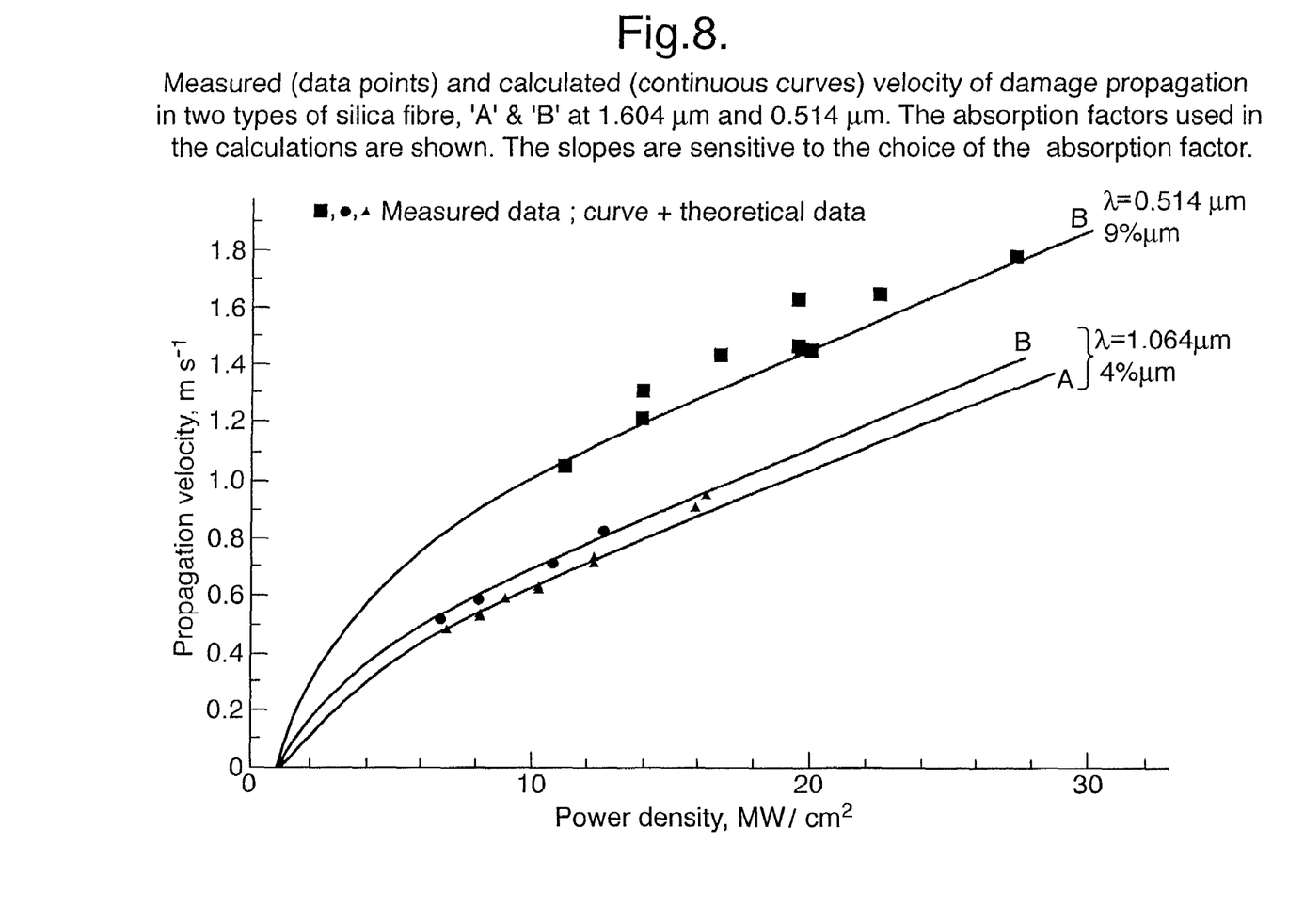
FIG. 8: shows how the velocity of catastrophic damage propagation varies as a function of the power density of the signal transmitted in an optical fibre, for three fibres A, B and C.

FIG. 7 shows the velocity of catastrophic damage propagation for each fibre A and B with respect to the optical power of the signal input to the fibre by the Nd:YAG and argon lasers, respectively. FIG. 7 shows that in the region of the graphs shown, that is for input powers between 1 Watt and 2.5 Watts, there exists a linear relationship between the input power and the velocity of propagation of catastrophic damage. The nature of the linear relationship is seen to vary however depending on the fibre characteristics shown above in Table 1.

With respect to FIG. 8, there is shown a plot of measured (data points) and calculated (continuous curves) for the velocity of the propagation of catastrophic damage as a function of the power density of the optical signal transmitted by the optical fibres A and B. Fibre A was operated at 1.064 micrometers using an absorption of 4% micrometers$^{-1}$ (corresponding to an absorption coefficient of $4 \times 10^2$ cm$^{-1}$). Fibre B was operated at 1.064 micrometers using an absorption factor of 4% micrometers$^{-1}$ (corresponding to an absorption coefficient of $4 \times 10^2$ cm$^{-1}$). Fiber B was also operated at 514 nanometers using an absorption factor of approximately of approximately 9% micrometers$^{-1}$ (corresponding to an absorption coefficient of $9.4 \times 10^2$ cm$^{-1}$). The absorption factor of the optical fibre varies as a function of the temperature of the optical fibre. This relationship is has been investigated in Kashyap et al, "Heat flow modelling and visualisation of catastrophic self propagating damage in single mode optical fibres at low powers", 28$^{th}$ Annual Boulder Damage Symposium, Laser induced damage in optical materials 1996, SPIE Volume 2966, pages 586–591. The absorption factor has an extinction coefficient with an Urbach tail, as discussed in Urbach F, Phys. Rev 92, 1324, 1953, meaning that the absorption coefficient at any given temperature is a function of photon energy, and thus wavelength of propagating optical signal. Hence, for an optical signal having a wavelength of 1.064 micrometers, the absorption coefficient is $4 \times 10^2$ cm$^{-1}$, and for an optical signal having a wavelength of 514nanometers, the absorption coefficient is $9.4 \times 10^2$ cm$^{-1}$. It is seen from FIG. 8 that the linear relationship, as seen by the slope of the graph, is affected by the choice of the absorption factor.

It was found that the propagation velocity of catastrophic damage varies as a function of the power density of the optical signal transmitted by each optical fibre.

Further, for a fixed power density, the velocity of damage propagation increases as a function of the mode field radius. Increasing the mode field radius increases the heat production. The more heat that is generated in the fibre as damage propagates increases the velocity of damage propagation. However, with reference to FIG. 8, it is seen that the mode field radius for fibre B operating at 514nanometers is 3.30 micrometers, smaller than for fibres A and B operating at 1.064 micrometers. Yet for a given power density the velocity of propagation is higher than for fibres A and B operating at 1.064 micrometers. This can be explained with reference to the absorption coefficient. Even though the 514 nanometer signal as transmitted in fibre B has a lower mode field radius and generates less heat, the heat that is generated is more readily absorbed thus increasing the velocity of propagation. As mentioned previously the absorption coefficient varies as a function of the wavelength. The shorter wavelength 514 nm signal resulting in a higher absorption coefficient in fibre B than the longer wavelength 1.064 micrometer signal in fibre B.

It is seen that the relationship between power density and propagation velocity of catastrophic damage is not linear over the entire calculated range of 0 to 30 MWcm$^{-2}$ shown in FIG. 8. The relationship does appear to be linear for power densities of the order of between 8–30 MWcm$^{-2}$, i.e. for higher power densities. For power densities in the order of approximately 0–8MWcm$^{-2}$, i.e. at lower power densities, the relationship is not linear. At lower power densities heat spreads from the core of the optical fibre before it can be absorbed into the region of propagating damage to thus cause the damage to propagate further. This effect is responsible for the calculated curvature of the graph shown in FIG. 8. For those fibres A and B operating under the conditions given above, this effect produces a threshold power density below which catastrophic damage cannot propagate. Further, at a particular power density, observed in experiment, the damage remains stationary. This occurs where the heat loss equals the heat input. For the examples shown, the calculated threshold below which catastrophic damage cannot propagate is approximately 1 MWcm$^{-2}$, which corresponds to an optical power of approximately 0.125 W average for single mode system fibre. Thus, the concept of sustaining power density is established. There exists a critical power density below which the propagation of catastrophic damage will stop. The mode field transformer is designed to decrease the power density to below this critical threshold.

As mentioned previously the region of the graph at higher power densities exhibits a more linear characteristic. In particular, the slope of each line is approximately equal for both fibres A and B, and fibre B operating at both wavelengths. From this it is deduced that the energy density required for catastrophic damage to propagate is a constant, $5 \times 10{-}12 m^{-3} J^{-1}$, for those fibres A and B and under those operating conditions given.

It will be understood that the threshold value and energy density value identified above will vary depending on many factors including the fibre construction and configuration, the operating wavelength of the optical signal. Further, for multimode fibres these values will differ again.

In addition to those stimuli discussed above, it has been found that catastrophic damage propagation may be initiated in an optical fibre carrying a high power optical signal by subjecting the fibre to various external stimuli. Such stimuli may include breaking the optical fibre and bringing it in contact with an absorbing surface to cause localised heating to the broken end, or subjecting the fibre to heat. It has been found, refer to Electronic Letters, 2 Mar. 2000, vol. 36, no. 5, pages 414–416, that it is not necessary to break the fibre to initiate catastrophic damage. Damage may be initiated by bending the fibre. Once catastrophic damage has been initiated in the fibre, it requires a source of energy to fuel its propagation. It has been found that optical signals having an optical power of the order of 1 Watt or more may fuel the propagation of damage along the fibre. The damage will then propagate in a direction towards the source of optical power.

The present invention provides means to halt the propagation of catastrophic damage in an optical fibre. This is achieved by providing a mode field radius transformer at locations along an optical route where it is desired to prevent optical damage from propagating further. Bearing in mind that the optical damage propagates in an upstream direction towards the source of optical power, the locations, or identified sites, may, for example be directly downstream from expensive route components such as amplifiers or optical sources. Alternatively, those locations may be at points within an optical route where one route operator relinquishes control of that route to a third party. This is the situation where one operator leases dark fibre within their own route to another operator.

The mode field radius transformer disposed at identified sites functions to increase the mode field radius of the optical signal transmitted on the optical power, so as to bring the power density to below that required to sustain catastrophic damage propagation. Thus, in the systems described the mode field radius transformer increases the mode field radius of the optical signal so as to bring the power density to below 1 MWcm$^{-2}$, which is the approximate value of the sustaining power density described above.

The mode field radius transformer may include various means. The mode field radius transformer includes a section of optical fibre. The section of optical fibre includes a waist portion. Preferably, the waist portion has a diameter or cross-sectional area that is lower than the diameter or cross sectional area of the system fibre or of the fibre pigtail. The section of optical fibre is spliced using conventional techniques to system fibre or to a fibre pigtail. The section of optical fibre, the system fibre and the fibre pigtail preferably include a glass composition. The section of optical fibre included in the mode field radius transformer, preferably, in addition to the waist portion may include, in addition two further portions of optical fibre between which the waist portion is disposed. The diameter or cross sectional area of the waist portion is lower than the diameter or cross sectional area of the two portions between which the waist portion is located.

The mode field radius transformer, as mentioned previously is formed by heating and drawing a section of optical fibre. The cross sectional area along the longitudinal axis of the drawn section of optical fibre varies in accordance with the conditions under which it is formed. However, the cross sectional area is at a maximum at the points at which the section of optical fibre is held, and is at a minimum between the two end portions. The cross sectional area may vary continuously along the longitudinal axis from the waist portion to each end.

The mode field radius transformer may also be described as including a tapered optical fibre.

However, it may take other forms. For example, at the identified location, a suitably dimensioned air gap provided between two fibre ends which have been processed to include a spherical lens will also function to transform the mode field radius of an optical signal transmitted by one of the fibres.

The inventors of the present invention have realised that a section of optical fibre may be dimensioned so that when an optical signal is transmitted through that section, its mode field radius is increased. Thus, for a given optical power, if the mode field radius is increased, the optical density will be decreased. The amount the mode field radius increases can be controlled by selecting the dimensions of the tapered portion. Using the examples given above, the tapered section is dimensioned that the optical density in the tapered section is less that 1 MWcm$^{-2}$, which is the approximate value of the sustaining power density described above.

The inventors of the present invention have further realised that if mode field transformers are disposed at locations in an optical route their presence will not affect communications along that route. It has also been observed that an optical signal passing through a mode field transformer does not suffer substantial optical power losses as a result of transmission through a mode field transformer. However, in the event that catastrophic damage does propagate to the location where the mode transformer is situated, it will be halted at that location. Preferably, locations are identified by taking into consideration locations of route components within the optical route, locations where damage may be initiated, points in the route where the route operator may want to relinquish control of that route, and the direction of propagation any catastrophic damage is likely to take, i.e. towards an optical source. By identifying locations using these criteria, route components are protected, and any damage that may occur to the route is arrested as soon as possible.

As mentioned above, the mode field transformer preferably takes the form of a section of optical fibre. The type of fibre chosen for the section will depend on particular application. However, in principle any type of fibre may be used for the section.

It has been found that by controlling the dimensions of the section of optical fibre, in particular the diameter or cross section of a waist portion of the optical fibre section, the amount of optical power leaked from the waveguiding region can be controlled. For example, it has been found that by incorporating a tapered section having a diameter of 1 micrometer, the power density of an optical signal of optical power of the order of 1 Watt is reduced to below the threshold level required for catastrophic damage to occur. It is also known that for a section of optical fibre of diameter 20 micrometers, less than 1% loss of optical power occurs.

The optical fibre section is introduced into the optical route between system fibre. The section is spliced between system fibre by any conventional splicing method. The section is preferably disposed outside the container 14 within which is disposed an optical route component. However, the section may be disposed within the container 14. Preferably, the section of optical fibre 23 is disposed within a housing 25. Preferably at least a portion of the container 14 is disposed within the housing 25. The section of optical fibre includes a waist portion which has a smaller diameter than the system fibre or fibre pigtail. It also has a smaller cross sectional area than the ends of the section of optical fibre. Preferably, the section's diameter or cross sectional area is reduced to a point in the waist portion (or tapered) along its longitudinal axis. It is known to form waist portions in a section of optical fibre. Known techniques for reducing the cross sectional area or diameter of optical fibre, are for example, redrawing the fibre by heating a section and drawing it to elongate the heated region resulting in a gradual reduction in the diameter or cross sectional area (or tapering) between the end of the section of optical fibre and the waist portion. In granted patent EP0555847, the sections of tapered fibre formed, are further formed into miniature fibre optic bend devices. Such miniature bends are incorporated into component design in order to reduce the size of the component, and hence the container required to package the component.

Figure 2:
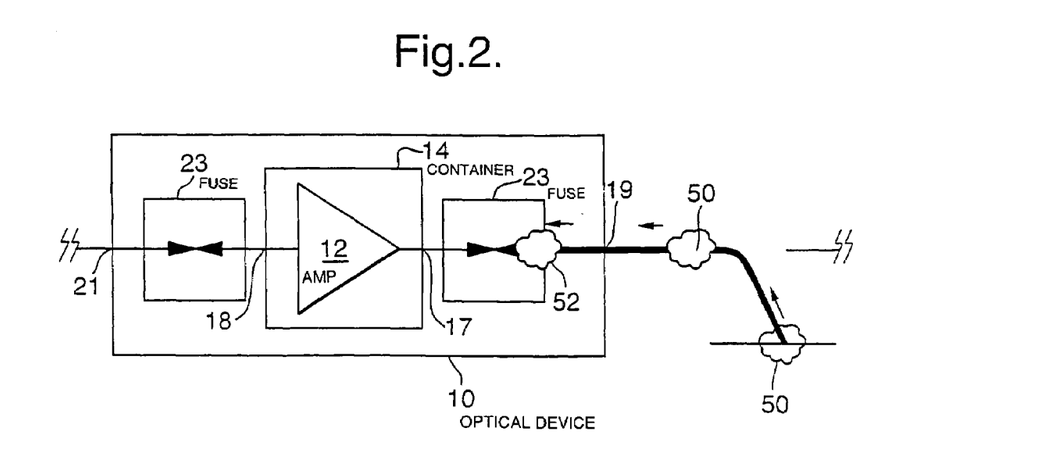
FIG. 2: shows an optical device including an optical amplifier according to the present invention subject to catastrophic damage.

FIG. 2 shows an optical device including an optical amplifier according to the present invention subject to catastrophic damage. A section of tapered optical fibre is disposed between the output 17 of the amplifier component 12 and the output 19 of the optical device 10. An optical signal of approximately 1 Watt or more is output from output 17 of the contained amplifier 14 in a downstream direction via the section of tapered optical fibre towards the output 19 of the device 10. As mentioned above, an optical power of this order of magnitude is sufficient to fuel the propagation of any self propagating self focussing damage that may have been initiated. Such damage will propagate towards the source of the fuel. In the device shown in FIG. 1, the source of the "fuelling" optical signal is the transmitter (not shown) and the amplifier 12.

The optical fibre section is dimensioned, so that when an optical signal passes through a first narrowing part of the section the mode field radius of the optical signal is increased. As a result, the amount of optical power confined by the waveguiding region is reduced in this section as the section narrows, that is as the diameter or the cross sectional area of the section of fibre become smaller. The diameter or crossectional area of the waist portion is reduced with respect to the ends of the section of optical fibre, or the system fibre or fibre pigtail, so that at the point along the waist portion having the lowest diameter or cross sectional area, the mode field radius is increased so that the power intensity falls below the threshold required to sustain propagation of catastrophic damage. When the optical signal passes through a broadening part of the portion, the mode field radius is decreased. As a result, the amount of optical power confined by the waveguiding region is increased, and the optical density increases. There is no significant power lost by an optical signal passing through the section of optical fibre, including the waist portion. The dimensions of the waist portion are chosen so that the optical power confined to the waveguiding region within at least part of the waist portion is below the threshold discussed above for supporting self propagating self focussing damage. Thus, the "fuel" supplied to propagating damage that reaches the tapered section 23 will not be sufficient to support further propagation and the damage is arrested at the waist portion. In the device shown in FIG. 1 this means that fibre extending from the output 19 upto and including part of the waist portion 23 will be irrevocably damaged, but that the damage will be arrested at the waist portion and the components upstream of section 23 including the components disposed in container 14 will remain undamaged.

It will be understood that the optical fuse 23 has many applications, and may, for example, be used to protect any optical components that may be subject to catastrophic damage, including, for example, transmitters, pump lasers, single module amplifiers, such as that shown in FIG. 1 and multiple module amplifiers. As well as being applicable to fibre amplifiers, the fuses of the present invention are applicable in semiconductor optical amplifiers (SOA). The most important cost consideration in the design of an SOA is the packaging of the device. SOAs include a semiconductor laser chip typically provided with antireflective coating on both facets. The packaging costs arise because the chip requires active alignment and laser welding of the chip with input and output fibres. Thus, protecting the packaged amplifier is a major concern.

One advantage of deploying optical fuses is that expensive components such as those listed above may be protected at low cost.

Figure 3:
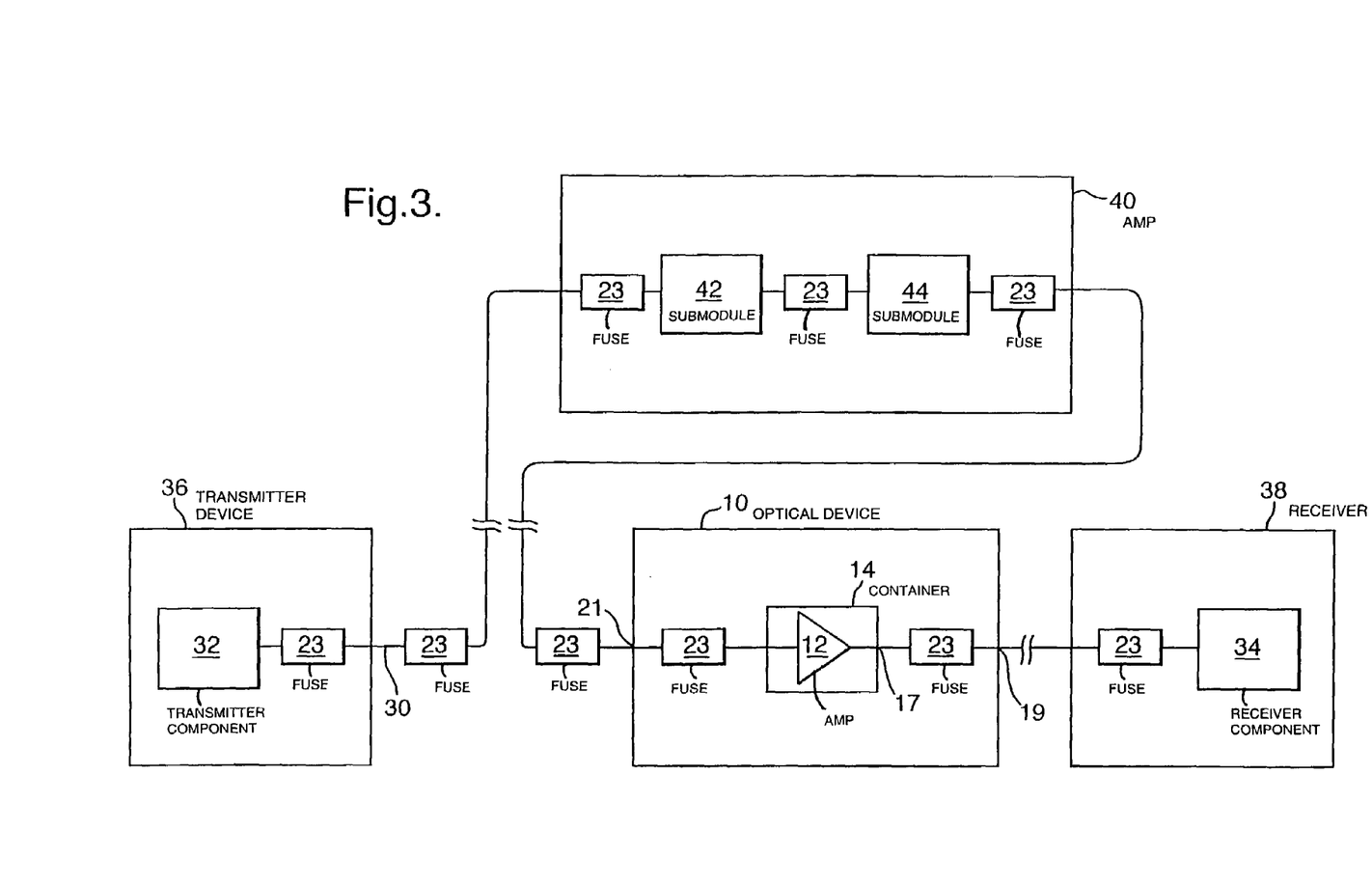
FIG. 3: shows an optical communications route including optical devices according to the present invention.

FIG. 3 shows an optical communications route including optical devices according to the present invention. The optical communications route shown in FIG. 2 includes route components 32, 12, 34, 42 and 44 protected by optical fuses 23. In particular, an optical transmitter device 36 includes a transmitter 32 housed in container 32, and an optical fuse 23. In the event that catastrophic damage should propagate into housing 36, optical fuse would function as described above to halt the catastrophic damage before it reaches the transmitter component 32. The optical amplifier 12 housed in container 14 represents a single module amplifier, and is protected by optical fuse 23 as described above in FIG. 1. Similarly, multiple module amplifiers 40 can also be protected by optical fuses from catastrophic damage. Multiple module amplifier 40 includes a first submodule 42 and a second submodule 44. Each submodule 42 and 44 is protected by optical fuses disposed at locations upstream and downstream of each submodule. In the event that catastrophic damage is initiated either between the submodules or in the second submodule and should propagate towards the first submodule 42, a fuse is disposed between the submodules.

As discussed above, damage initiated will propagate in a direction towards the source of the optical power. In the route shown in FIG 3, the source of the optical power is the transmitter component 32. Thus, damage will generally propagate towards the transmitter. Thus, it will be understood that it is unlikely that damage is likely to occur to a receiver component 34. However, should damage be initiated in the receiver component, a fuse may preferably be provided near the input of the receiver to protect optical fibre between receiver 38 and amplifier component 12.

Figure 4:
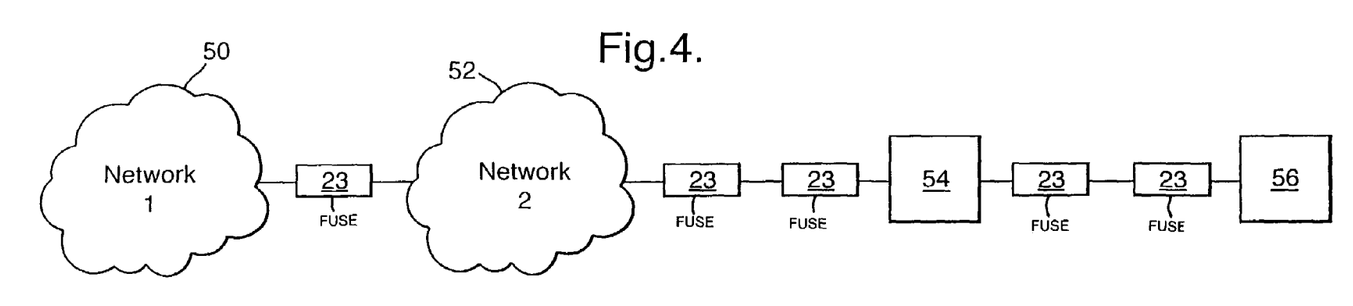
FIG. 4: shows an optical communications route including two networks.

With reference to FIG. 4, it will be understood that further route components of an optical route that may be required to be protected are optical route fibres which carry optical signals between other route components, such as the transmitter 32, amplifiers 14, 42, 44 and the receiver 34. As mentioned previously, should catastrophic damage occur to an optical route, it may destroy optical fibre several kilometers long. Such disruptions to an optical route are both expensive to repair and represent lost data, lost revenue and an increased burden on remaining routes of an optical network while the damaged optical fibre is being replaced. In particular, communications routes may include components belonging to different networks. A route may originate in network 1 (50) and may terminate in network 2 (52). Yet networks 1 (50) and 2 (52) may be operated by different network operators. In such situations, the network operator operating network 1 (50) may want to protect his network from catastrophic damage that may be initiated in network 2 (52), yet may propagate towards network 1 (50). Such protection is afforded by providing an optical fuse 23 between networks 1 (50) and 2 (52).

Further, it may be the situation that a network or route operator may wish to lease fibre between one network 2 and a cabinet 54, or also between a cabinet 54 and a customer's premises 56. In these and other similar situations within parts of a network, it is envisaged that any deployed system fibre may be provided with mode field transformers at its ends. Typically, in an urban area the deployed fibre may be anything from over approximately 100 meters long. If necessary, for example, where a cabinet is only a very short distance from a customer's premises, the deployed system fibre may be less than 100 m.

A further application for the optical fuses of the present invention is that network operators may lease dark fibre (that is fibre currently not being used for the transmission of optical signals) to other licensed operators. The dark fibre, once leased moves out of the direct control of the lessor. However, such dark fibre may be connected at locations within a network to fibre used by the lessor or other third parties. In such circumstances, where usage of optical fibre may not fall under the direct control of the lessor, it is important that damage that may occur in the leased fibre does not propagate to parts of the network operated by the lessor or other third parties. To protect network fibre, the present invention provides that mode field transformers be deployed at points within the network where an operator may which to be protected from activity carried out in other parts of the network that are not under his control.

The skilled person will realise that there are various other locations where it may be desirable to locate optical fuses to protect optical route fibres, for example at locations where data is transferred from a private network to a public networks, or where data is transferred between one network owned by one network operator and a second network operator.

Figure 5:
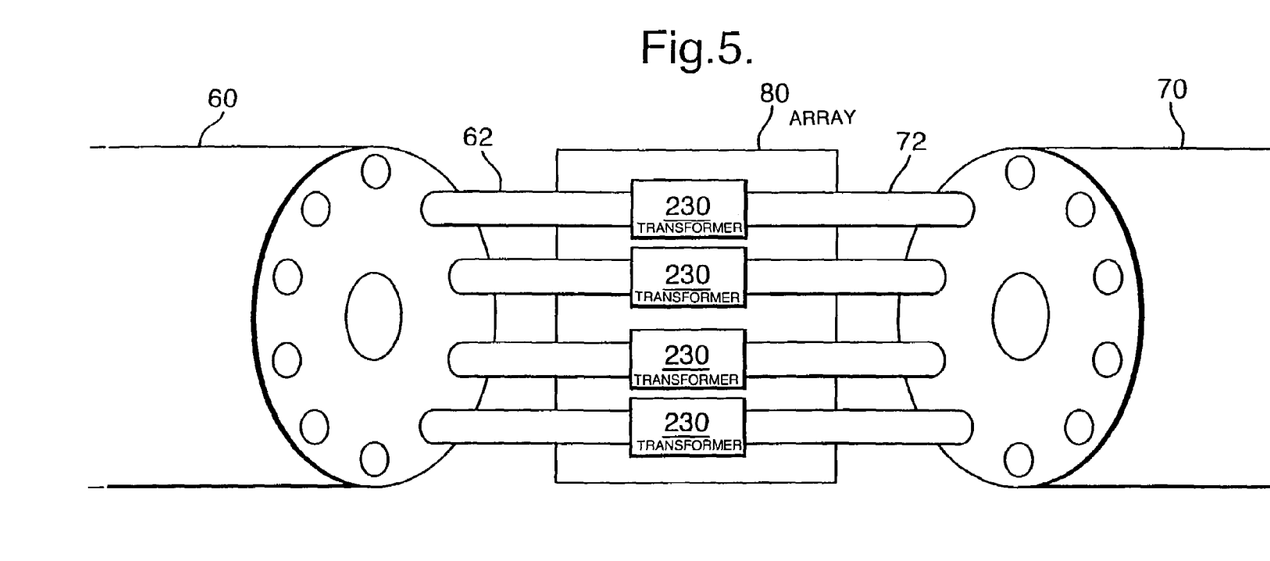
FIG. 5: shows a connectable array for connecting to two optical cables.

With reference FIG. 5, a connectable array 80 is shown which may be connected between two optical cables 60, 70 each optical cable having a plurality of optical fibres 62, 72. The array including a plurality of mode field radius transformers 230 as previously described. The array enables each optical fibre 62, 72 of cables 60, 70 to be protected from catastrophic damage that may propagate in any of optical fibres 62, 72. The array is configured so that each mode field radius transformer 230 is connectable with a respective optical fibre to thus protect each respective optical fibre.

Figure 6:
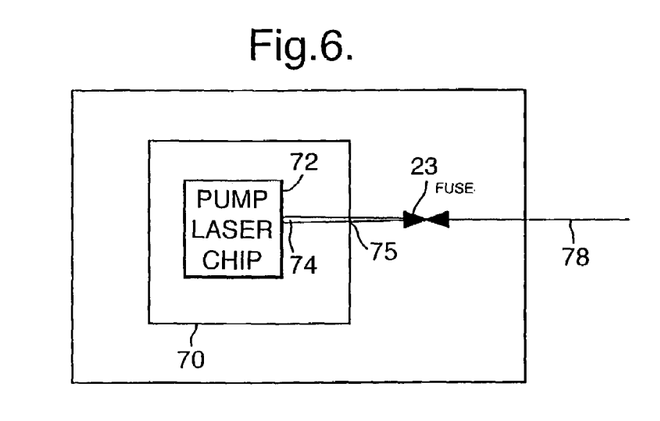
FIG. 6: shows an pump laser device according to the present invention.

With reference to FIG. 6, a pump laser 70 is shown. The pump laser includes a pump laser chip 72, a lensed fibre 74 which are both enclosed in a sealed container 70, the output 75 of the pump laser is connected to a laser pigtail fibre 78. A mode field transformer is disposed outside the sealed container 70 along the laser pigtail fibre. This arrangement has particular application for remote pump lasers for, in particular, submarine optical cables, where the pump laser is located on land and the laser pigtail fibre may be many kilometers long. Thus, in order to protect the relatively inaccessible laser pigtail fibre and more accessible, however costly pump laser from catastrophic damage, mode field transformers may be disposed at a location or locations along the laser pigtail fibre. The mode field transformers are not however limited for use only in remote pump lasers, but may also be incorporated into pump lasers for use in packaged amplifiers and optical sources.

It will be understood that the present invention has application in all areas of optical fibre technology where an optical fibre is subject to high optical power. These applications may range from laser surgery to industrial cutting and welding using a laser. For example, one particular example would be laser eye surgery to correct for myopia, where an optical fibre is used to deliver a high power optical beam to the cornea.

The invention claimed is:
1. An optical communication system comprising:
an optical communications route comprising system fiber or a laser pigtail fiber having a given mode field radius at an operating wavelength of the system,
an optical route component for performing a function within the optical system, said optical route component forming part of the optical communications route and being connected to the system fiber or a laser pigtail fiber, and enclosed in a sealed container,
the optical route component providing an optical output which passes along the system fiber or the laser pigtail fiber from the container, the output of the optical route component passing through a mode field transformer and thence along the system fiber or the laser pigtail fiber, the mode transformer including a section of optical fiber disposed at a location downstream of said container and serving to increase locally the mode field radius at said wavelength, the optical system being operated with an optical power density in the system fiber or the laser pigtail fiber above a level at which optical power induced damage can propagate in the system fiber or the laser pigtail fiber, the mode transformer reducing the optical power density for said given power level such that within the mode transformer the power density is reduced below the threshold level, so that in the event that optical power induced damage occurs in the system fiber or the laser pigtail fiber downstream of said mode transformer is prevented from propagating into the optical route component.

2. A system according to claim 1, wherein the mode transformer and the system fiber or laser pigtail fiber are made of glass.

3. A system according to claim 1, wherein the section of optical fiber included in the mode transformer includes a waist portion, wherein the diameter or cross sectional area of the waist portion is smaller than the diameter or cross sectional area of the system fiber or pigtail fiber.

4. A system according to claim 3, wherein said waist portion is symmetrically disposed about the longitudinal axis of the section of optical fiber included in the mode transformer.

5. A system according to claim 1, wherein at least part of said container and said mode field transformer are disposed within a housing.

6. A system according to claim 5, wherein said mode field transformer is readily accessible within said housing.

7. A system according to claim 1, wherein said optical component includes an optical transmitter or an optical receiver or a fiber amplifier or a semiconductor amplifier or an arrayed waveguide grating or a planar silica waveguide.

8. An optical device for use in a system according to claim 1, said device including an optical route component for performing, in use, a function within the optical system, and being enclosed in a sealed container, the optical route component having a fiber pigtail for connection to a downstream optical fiber of said system, the optical route component providing an optical output having in said fiber pigtail a given mode field radius at an operating wavelength of said device;

the device further including a mode field transformer including a section of optical fiber, said mode field transformer being disposed at a location downstream of said container between said container and said fiber pigtail, said mode field transformer having a mode field radius at said wavelength substantially larger than said given mode field radius and being sufficiently large to reduce at said location the optical power density of said optical output to below the threshold level at which optical power induced damage can occur in said pigtail fiber downstream of said mode field transformer, thereby, in the event that optical power induced damage occurs in the pigtail fiber, preventing the damage from propagating into the optical route component.

9. A method of protecting an optical communications route carrying a high power optical signal from catastrophic damage caused by the propagation of optical power induced damage along said route, said method comprising:

identifying a site where optical power induced damage is likely to be initiated and the likely path of damage propagation, selecting a route component to be protected, disposed in said path, disposing a mode field radius transformer at a location in said optical communications route between said identified site and said selected component, the optical communications route having an optical fiber transmission path connecting said site and said component, the optical fiber having a given mode field radius at an operating wavelength of the signal, the power density of said optical signal in said fiber being at a level at which optical power induced damage can propagate in said fiber, said mode field radius transformer including a section of optical fiber to increase substantially the mode field radius with respect to said given mode field radius so that the optical power density in the mode field transformer is reduced to a level at which optical power induced damage cannot propagate through the mode field transformer, so that optical power induced damage will be halted at said location before reaching said component.

10. A method according to claim 9, wherein the section of optical fiber included in the mode field radius transformer includes a waist portion having a cross-sectional area which is smaller than a cross-sectional area of the optical fiber transmission path connecting said site and said component.

11. A method according to claim 9, wherein a cross-sectional area of a waist portion of the mode field radius transformer has a dimension so that an amount of optical power, necessary for the optical power density of the optical signal to be reduced below the level at which optical power induced damage cannot propagate through the mode field radius transformer, is leaked.

12. A mode field transformer including a section of optical fiber which provides a localized increase in mode field radius from that of adjacent system fiber to serve as a barrier to the propagation of optical power induced optical damage from the system fiber through the mode field transformer by decreasing optical power density to a level below which propagation of optical power induced optical damage is supported, the optical fiber of the mode field transformer including a waist portion having a cross-sectional area that is lower than the cross-sectional area of the adjacent system fiber.

13. A system according to claim 3, wherein the diameter or cross-sectional area of the waist portion has a dimension so that an amount of optical power necessary for the optical power density to be reduced below the threshold level is leaked.

14. An optical communications route comprising a deployed system fiber which is at least 100 meters in length, the system fiber having a given mode field radius at a given wavelength at which the fiber is designed to operate, said system fiber being provided with a mode field transformer at each end of said fiber, each mode field transformer having at said wavelength a mode field radius at least three times said given mode field radius;

wherein the mode field transformer includes a waist portion having a cross-sectional area which is smaller than the cross-sectional area of the system fiber.

15. A route according to claim 14, wherein the cross-sectional area of the waist portion has a dimension so that an optical power of an optical signal transmitted by the optical communications route is leaked.

16. A plurality of mode field radius transformers disposed in an array, being arranged in use, so that each mode field radius transformer is connectable or spliceable with a respective system fiber in which at a given wavelength the mode field radius of an optical signal is x, each mode field radius radius transformer being arranged to increase the mode field radius of said optical signal, with respect to x, so that the power density of said optical signal in said mode field radius transformer is reduced to a level below the threshold required for optical power induced damage to propagate within the mode field radius transformer;

wherein at least one of the mode field radius transformers includes a waist portion having a cross-sectional area which is smaller than the cross-sectional area of the respective system fiber connected or spliced with that at least one mode field radius transformer.

17. A plurality of mode field radius transformers according to claim 16, wherein at least one mode field radius transformer includes a waist portion having a cross-sectional area with a dimension so that an amount of optical power necessary for the optical power density to be reduced to a level below the threshold is leaked.

18. A method of protecting an optical communications route carrying a high power optical signal from the propagation of optical power induced damage along the route, the route including an optical device including a route component for performing a function within the optical route, said route component being housed in a container, said method including:

providing an optical fiber section at a location in said optical communications route outside said container, the optical fiber section being so dimensioned as to decrease the optical power density within said optical fiber section to a level below that at which catastrophic damage propagation is supported, so that optical power induced damage propagating in the route immediately downstream of said location will be halted at said location before reaching said container;

wherein the dimension of the optical fiber section to decrease the optical power density within the optical fiber section to a level below that at which catastrophic damage propagation is supported has a cross-sectional area which is smaller than the cross-sectional area of another optical fiber section in the optical communications route.

19. An optical communications system comprising:
a source of optical power;
an optical communications route having a first optical fiber portion, a mode field radius transformer and a second optical fiber portion, the first optical fiber portion receiving an optical communications signal from the source of optical power and passing the optical communications signal through the mode field radius transformer to the second optical fiber portion in a downstream direction;
wherein the mode field radius transformer transforms a mode field radius of the optical communications signal and includes a waist portion having a cross-sectional area which is smaller than the cross-sectional area of the first and second optical fiber portions.

20. A system according to claim 19, wherein the cross-sectional area of the waist portion is sufficiently small so as to halt at the waist portion any self-focusing damage which reaches the waist portion.

21. A system according to claim 19, wherein the cross-sectional area of the waist portion has a dimension so that optical damage propagating in an upstream direction towards the source of optical power is halted by the mode field radius transformer.

22. An optical communications system comprising:
a source of optical power;
an optical communications route having a first optical fiber portion, a mode field radius transformer and a second optical fiber portion, the first optical fiber portion receiving an optical communications signal from the source of optical power and passing the optical communications signal through the mode field radius transformer to the second optical fiber portion in a downstream direction;
wherein the mode field transformer includes a waist portion having a cross-sectional area so that an amount of optical power is leaked so as to reduce the power density of the optical signal to a level below a threshold required for propagation of optical power induced damage to occur.

23. A system according to claim 22, wherein the cross-sectional area of the waist portion has a dimension so that the optical power induced damage propagating in an upstream direction towards the source of optical fiber is halted by the mode field radius transformer.

* * * * *